United States Patent [19]

Watson et al.

[11] 4,421,640
[45] Dec. 20, 1983

[54] METHODS FOR SEPARATING HYDROCARBONS BY LIQUID EXTRACTION

[75] Inventors: James M. Watson, Big Spring, Tex.; Jacques F. J. Grootjans, Leefdaal; Luc F. L. N. Delorme, Brussels, both of Belgium

[73] Assignee: Cosden Technology, Inc., Dallas, Tex.

[21] Appl. No.: 349,398

[22] Filed: Feb. 16, 1982

[51] Int. Cl.³ .............................................. C10G 21/20
[52] U.S. Cl. .................................... 208/326; 585/860
[58] Field of Search ......................... 208/326; 585/860

[56] References Cited

U.S. PATENT DOCUMENTS

| | | | |
|---|---|---|---|
| 2,771,494 | 3/1953 | Weedman | 585/860 X |
| 2,849,396 | 8/1958 | Nelson | 208/326 |
| 3,157,592 | 11/1964 | Fuerst et al. | 208/326 |
| 3,210,259 | 10/1965 | Cornell et al. | 208/326 |
| 3,617,535 | 11/1971 | Weitz et al. | 208/326 X |

FOREIGN PATENT DOCUMENTS

| | | | |
|---|---|---|---|
| 704248 | 2/1965 | Canada | 585/860 |
| 2115858 | 10/1972 | Fed. Rep. of Germany | 585/860 |
| 7215610 | 5/1973 | Netherlands | 585/860 |
| 1169113 | 10/1969 | United Kingdom | 208/326 |

Primary Examiner—Delbert E. Gantz
Assistant Examiner—Glenn Caldarola
Attorney, Agent, or Firm—Russell H. Schlattman

[57] ABSTRACT

Aromatic hydrocarbons are separated from a mixture thereof with paraffinic hydrocarbons by solvent extraction with N-(2-hydroxyethyl)-2-pyrrolidone containing a minor amount of water at specified elevated temperatures and pressures. Temperature variations within the specified range have little effect on the loading capacity and selectivity of the solvent thus greatly simplifying process control.

5 Claims, No Drawings

METHODS FOR SEPARATING HYDROCARBONS BY LIQUID EXTRACTION

TECHNICAL FIELD

This invention relates to the separation of liquid hydrocarbons by solvent extraction. More particularly, the present invention relates to such an extraction process employing a solvent comprising N-(2-hydroxyethyl)-2-pyrrolidone (hereinafter referred to as HEP).

BACKGROUND OF THE INVENTION

It is known that hydrocarbon mixtures comprising paraffinic and aromatic compounds can be separated by liquid extraction through the use of an organic solvent. The selection of an organic solvent for the particular extraction process must take into consideration a number of factors. Such factors include selectivity, capacity, recoverability, density, interfacial tension, corrosivity, chemical reactivity and stability, viscosity, toxicity and cost.

The use of N-hydroxyalkylpyrrolidones for separating aromatics and paraffinic compounds has previously been disclosed in U.S. Pat. No. 3,157,592. The process there disclosed is carried out at atmospheric pressure and at temperatures in the range of 5° to 60° C.

In most processes for the solvent extraction of aromatics contained in a mixture with paraffinic compounds, separation of the aromatics from the solvent usually requires distillation at an elevated temperature. In such a process, operating the extraction step of the process at an elevated temperature maximizes the efficient use of energy. Solvent selection for use at elevated temperatures poses several problems. Higher temperatures, while increasing the loading capacity of the solvent, tend to decrease its selectivity. In such an extraction process as this, water is commonly used to control selectivity. However, while increasing the water content will increase the selectivity of the solvent, the loading capacity of the solvent is simultaneously reduced. As a result of these conflicting effects, as well as the other previously mentioned factors which must be considered, very few solvents have really been found suitable for the efficient extraction of aromatics contained in a mixture with paraffinic compounds at elevated temperatures.

Accordingly, it is an object of this invention to provide an improved process for treating a hydrocarbon mixture to selectively separate the aromatic and paraffinic components thereof by a liquid-liquid solvent extraction of the aromatics at elevated temperatures. Other objects will become apparent from the description of the invention.

DISCLOSURE OF THE INVENTION

According to the present invention, a liquid hydrocarbon mixture of aromatic and paraffinic components is treated by mixing the mixture with HEP containing a minor amount of water at a temperature in the range of from about 225° F. (107° C.) to about 325° F. (162° C.) and a pressure of from about 85 psia (586 kilopascals) to about 310 psia (2137 kilopascals) and then allowing the resultant mixture to separate into a raffinate phase and an extract phase, the latter being rich in the aromatic hydrocarbon components of said hydrocarbon mixture. The aromatic hydrocarbon components can be recovered by any conventional method, e.g., by distillation.

DESCRIPTION OF THE PREFERRED EMBODIMENT

The equipment to demonstrate the utility of HEP in the process of this invention consisted of a sealable metal vessel having a volume of approximately one liter. The vessel was equipped with a mechanical agitator and sampling lines equipped with sightglasses to permit withdrawing samples from the upper layer (raffinate phase) and lower layer (extract phase).

In each extraction test, a weighed amount of each component was added to the vessel, the total volume of the resultant mixture being approximately one liter. The vessel was sealed, pressurized to the desired level and placed in a constant temperature bath maintained at the desired test temperature level. The mixture was stirred with the mechanical agitator for one half hour at the desired test temperature and pressure.

Following agitation for one half hour the agitation was stopped and the mixture allowed to settle for at least one half hour. The liquid level and the interphase were then read in the sightglasses, the sample lines then purged and samples of the top and bottom phases collected. The hydrocarbon and water content of the two phases was determined by chromatographic analysis. Hydrocarbons were separated from the solvent by distillation.

Tests were run over a wide temperature and pressure range, employing hydrocarbon mixtures having a variety of aromatic and paraffinic components, using HEP containing varying amounts of water. The previously mentioned analyses permitted a determination of the loading capacity of the solvent for the aromatic component as well as an evaluation of the selectivity of the solvent by comparing the concentration of the aromatic component in the solvent rich phase with the concentration of the aromatic component in the solvent lean phase, both on a solvent free base.

Solvent loading capacity for the aromatic component is an important characteristic for any extraction solvent. The excellent loading characteristics of HEP containing a minor amount of water have been demonstrated using a hydrocarbon mixture of benzene and n-hexane. The test method previously described was employed, maintaining extraction conditions at 200 psia (1379 kilopascals) and 275° F. (135° C.). The solvent was HEP containing varying amounts of water. Loading capacity of the solvent was expressed as the weight percent of the amount of solvent used represented by the weight of aromatics recovered. The following Table 1 sets forth the loading capacity realized when using a mixture of components in the ratio of 327 g. benzene, 247 g. n-hexane, 383 g. of HEP (including water). Water is expressed in terms of weight percent of total solvent composition.

TABLE 1

| Solvent | Loading Capacity |
| --- | --- |
| HEP + 1.0% water | 31% |
| HEP + 5.1% water | 25% |
| HEP + 11.9% water | 18% |

The foregoing Table 1 clearly indicates the effect of water content of the solvent on loading capacity. Selectivity is also effected by water content of the solvent. The following Table 2 illustrates this by setting forth typical coordinates of points on a plot of the aromatic content of the solvent rich phase vs. the aromatic content of the solvent lean phase (both on a solvent free basis). The hydrocarbon mixture was again benzene and n-hexane, with extraction conditions being 275° F. (135° C.) and 200 psia (1379 kilopascals).

TABLE 2

| Solvent | Wt. % of benzene in extract phase | Wt. % benzene in raffinate phase |
|---|---|---|
| HEP + 1.0% water | 73% | 40% |
| HEP + 5.1% water | 78% | 40% |
| HEP + 11.9% water | 82% | 40% |

The temperature at which an extraction process is carried out is generally recognized as an important factor. Generally, as extraction temperatures are increased, loading capacity of the solvent will increase but selectivity will decrease. In the instant case, however, it has been found that temperature variations in the elevated temperature range at which this extraction process is conducted, do not have a material effect on the process. Thus, control of the process is greatly simplified. Illustrative of this phenomenom are the results set forth in Tables 3 and 4.

In this series of runs, solvent composition was kept constant, viz., HEP+5.1% water. Pressure was maintained at 200 psia (1379 kilopascals). Extraction temperature was varied from 260° F. (127° C.) to 290° F. (143° C.). Test runs were conducted as previously described and loading capacity and selectivity determined and reported as in Tables 1 and 2. Table 3 sets forth the loading capacity obtained at various temperatures and Table 4 sets forth the selectivity obtained at various temperatures. The hydrocarbon mixture was again benzene and n-hexane.

TABLE 3

| Extraction Temperature | Loading Capacity |
|---|---|
| 260° F. (127° C.) | 26% |
| 275° F. (135° C.) | 25% |
| 290° F. (143° C.) | 25% |

Considering the reproducibility of these tests, the aforementioned loading capacities can be considered to be essentially the same.

TABLE 4

| Extraction Temperature | Wt. % of benzene in extract phase | Wt. % of benzene in raffinate phase |
|---|---|---|
| 260° F. (127° C.) | 78% | 40% |
| 275° F. (135° C.) | 78% | 40% |
| 290° F. (143° C.) | 74% | 40% |

Again, considering the reproducibility of these tests, the results indicate little variations in selectivity within the temperature range specified.

The utility of HEP containing minor amounts of water in the novel extraction process of this invention is further enhanced by its properties at elevated temperatures. Metal coupons of 304 stainless steel and carbon steel were immersed in HEP containing minor amounts of water for a period of 120 days at 392° F. (200° C.). No detectable corrosion was observed.

No significant changes in viscosity or color formation were noted in HEP containing minor amounts of water after being maintained at 392° F. (200° C.) for 120 days.

Aromatics contained in solvent rich phase can be conveniently separated therefrom and recovered by simple distillation or steam stripping. No fatal azeotropes were found that would interfere with such a recovery process and no foaming problems were encountered.

The novel process of this invention has been found applicable with hydrocarbon mixtures containing a wide variety of aromatic and paraffinic components. Such components include, in addition to benzene and n-hexane, toluene, xylenes, ethylbenzene, cyclopentane, methylcyclopentane and isohexane. The aromatics in depentanized reformate have also been satisfactorily extracted and recovered.

The water content of the solvent employed in the extraction process of this invention is subject to variation. Only a minor amount of water is necessary. Preferably the solvent contains from about 1 to about 20 percent by weight of water. Particularly advantageous results are obtained when the solvent contains from about 4% to about 12% by weight of water. The foregoing water contents are based upon the weight of the total solvent composition. The temperatures employed in the process of this invention can vary from about 225° F. (107° C.) to about 325° F. (162° C.), with temperatures in range of from about 250° F. (121° C.) to about 275° F. (135° C.) being particularly preferred. The pressure at which the extraction process is carried out can vary from about 85 psia (586 kilopascals) to about 310 psia (2137 kilopascals), with pressures in the range of from about 100 psia (690 kilopascals) to about 200 psia (1379 kilopascals) being preferred.

The extraction process itself can be carried out as a batch operation as described herein or as a continuous operation in a conventional liquid-liquid extraction column. Packed columns are particularly advantageous. In such an operation, the selective solvent is continuously introduced into the upper end of the column and the hydrocarbon mixture is introduced into the central part of the column. The raffinate is continuously withdrawn from the top portion of the column above the solvent inlet, with the extract being continuously removed from the bottom of the column. The aromatics can be conveniently recovered from the solvent rich phase by distillation, with the solvent being recycled to the extraction column.

What is claimed is:

1. A process for treating a hydrocarbon mixture to selectively separate the aromatic and paraffinic components thereof which comprises mixing said hydrocarbon mixture with a selective solvent consisting essentially of N-(2-hydroxyethyl)-2-pyrrolidone containing a minor amount of water at a temperature in the range of from about 107° C. to about 162° C. under pressure of from about 586 kilopascals to about 2137 kilopascals, separating the resultant mixture into two phases to obtain a raffinate phase and an extract phase, the latter being rich in the aromatic hydrocarbon components of said hydrocarbon mixture.

2. The process of claim 1 wherein the selective solvent consists essentially of N-(2 hydroxyethyl)-2-pyrrolidone containing from about 1 to about 20 percent by weight of water based on total solvent composition.

3. The process of claim 2 wherein the mixing of the hydrocarbon mixture with the selective solvent is carried out at a temperature in the range of from about 121° C. to about 135° C. and a pressure in the range of from about 690 kilopascals to about 1379 kilopascals.

4. The process of claim 1 wherein the selective solvent consists essentially of N-(2-hydroxyethyl)-2-pyrrolidone containing from about 4% to about 12% by weight of water based on total solvent composition.

5. The process of claim 4 wherein the mixing of said hydrocarbon mixture with the selective solvent is carried out at a temperature in the range of from about 121° C. to about 135° C. and a pressure in the range of from about 690 kilopascals to about 1379 kilopascals.

* * * * *